United States Patent [19]

Jacobson et al.

[11] 4,444,745

[45] Apr. 24, 1984

[54] AEROSOL SOLUTIONS OF 1-NAPHTHYLMETHYLCARBAMATE

[75] Inventors: Norman A. Jacobson; Clayton W. Yoho, both of Racine, Wis.

[73] Assignee: S. C. Johnson & Son, Inc., Racine, Wis.

[21] Appl. No.: 472,896

[22] Filed: Mar. 7, 1983

[51] Int. Cl.³ .............................................. A01N 47/10
[52] U.S. Cl. ...................................... 424/45; 424/300
[58] Field of Search ......................... 424/300, 45, 264

[56] References Cited

U.S. PATENT DOCUMENTS

| | | | |
|---|---|---|---|
| 2,903,478 | 9/1959 | Lambrech | 424/264 X |
| 4,067,990 | 1/1978 | Dulat | 424/300 X |
| 4,382,078 | 1/1983 | Berkhoff et al. | 424/45 |

OTHER PUBLICATIONS

Chemical Abstracts 72, 77973p (1970); Nishimura et al.
Chemical Abstracts 57, 2356b (1962); Scott et al.

*Primary Examiner*—Leonard Schenkman
*Assistant Examiner*—Joseph A. Lipovsky

[57] ABSTRACT

Dimethylether ether has been found to be a good solvent for 1-naphthylmethylcarbamate. This allows the carbamate to be solubilized so that it can be sprayed from an aerosol container.

2 Claims, No Drawings

AEROSOL SOLUTIONS OF 1-NAPHTHYLMETHYLCARBAMATE

This invention relates to an insecticidal composition. More particularly, this invention relates to a solution of 1-naphthylmethylcarbamate, also known as carbaryl.

Carbaryl has been a commercially important insecticide and is used to kill insect pests in crops, forests, lawns, poultry and around pets. Because of the fact that prior to the present invention carbaryl has limited solubility in most common solvent or water, this material was used as a dust or wettable powder. Although carbaryl has high activity against insects, it has not been particularly suitable for use in aerosol compositions because of its lack of solubility in appropriate solvents, especially those solvents which can be safely handled by consumers and/or pest control operators such as chlorinated solvents.

Attempts to use carbaryl in aerosol sprays have failed because the insoluble carbaryl particles clog the aerosol spray nozzle, thereby rendering the aerosol container useless.

Surprisingly, it has been found that carbaryl has a high degree of solubility in dimethylether. Further, this carbaryl-dimethyl ether solution can be mixed with water and/or lower alcohols. Dimethyl ether is a material which is usable as a component in aerosol compositions.

OBJECTS AND ADVANTAGES

It is, therefore, the primary object of the present invention to provide a solution of carbaryl.

It is a still object of the present invention to provide an aerosol composition containing carbaryl in a solution.

It is a still further object of the present invention to provide a solution of carbaryl mixed with water and/or lower alkanols.

Still further objects and advantages of the composition of the present invention will become apparent from the following more detailed description thereof.

DETAILED DESCRIPTION

The composition of the present invention comprises a solution of 1-naphthylmethylcarbamate in dimethyl ether wherein the weight ratio of 1-naphthylmethylcarbamate to dimethyl ether is from 1:200 to 1:5.

Carbaryl is a commercially available insecticide available from Union Carbide. The method of manufacture of this material is described in U.S. Pat. No. 2,903,478. It has been found that carbaryl can be solubilized in dimethyl ether in a weight ratio of 1:200 to 1:5. Generally, the carbaryl will be present in amounts of from 0.5 to 20% by weight in a formulation. It is preferred, primarily, for economic and regulatory reasons, to use compositions including from 1 to 10% by weight carbaryl.

Dimethyl ether is a commercially available compound often used as a propellent in aerosol compositions. For this reason, it is possible to prepare an aerosol composition comprising solely dimethyl ether and carbaryl. In these two component products the dimethyl ether will comprise the other portion of the formula, i.e., from 99.5 to 80% by weight. However, it will be desirable to often include diluents or cosolvents so that the dimethyl ether will be present in an amount of from 99.5 to 15% by weight. Diluents which may be incorporated into the compositions might include other propellents such as propane, butane, isobutane, etc., lower alkanols such as methanol, ethanol, propanol, isopropanol, butanol and mixtures thereof, as well as mixtures of lower alkanols and water. These diluents can be present in an amount of from 0 to 70% by weight.

Although the composition can be described in terms of total weight percent, the truly critical relationships are the relative ratio of carbaryl to dimethyl ether. It has been found that clear solutions will result if the ratio of carbaryl to dimethyl ether is within the range of 1:200 to 1:5.

The compositions may also optionally include a small amount of surfactant. Suitable surfactants include the nonionic surfactants such as ethoxylated octyl phenols, etc. and certain anionic surfactants, etc.

The composition of the present invention can be prepared by placing the carbaryl in an aerosol container and pressure filling the dimethyl ether to this container. The carbaryl is sufficiently soluble in the dimethyl ether that on standing for a reasonable amount of time, the carbaryl is completely solubilized in the dimethyl ether.

The composition of the present invention will now be illustrated by the following examples which are for the purpose of illustration only and are in no way to be considered as limiting.

EXAMPLE 1

To an aerosol glass pressure bottle 1 gram of technical carbaryl was added and a 0.018×0.018 inch bottle valve was crimped on and 10 milliliters of dimethylether was pressure filled. This sample became clear, indicating complete solubility of the carbaryl at these levels. The composition contained within this pressure bottle was then sprayed and showed good sprayability.

EXAMPLE 2

The procedure of EXAMPLE 1 was followed, except that 20 milliliters of dimethylether was added to 1 gram of carbaryl. Again, the composition within the container became clear, indicating complete solubility of the carbaryl in the dimethylether.

EXAMPLE 3

Using the procedure of Example 1, a formulation having the following composition was prepared: 10% technical carbaryl (97.5%), 10% ethyl alcohol and 80% dimethyl ether. This composition, when packaged in an aerosol container, produced a composition having a pressure of 65 psig and formed a clear solution.

EXAMPLES 4–7

Using the procedure of Example 1, formulations were prepared having the compositions as shown in Table I:

TABLE I

| Example | 4 | 5 | 6 | 7 |
|---|---|---|---|---|
| Carbaryl Tech (97.5%) | 10 | 10 | 10 | 2 |
| Ethyl Alcohol | 10 | 10 | 10 | 50 |
| Water | 20 | 10 | 20 | 25 |
| Triton X-193[1] | — | — | 1.0 | — |
| Dimethyl Ether | 60 | 70 | 59 | 33 |
| Pressure (psig) | 65 | 65 | 65 | 40 |

[1]Triton X-193 is a proprietary mixture of anionic and nonionic surfactants available from Rohm & Haas, Philadelphia, PA.

Each of these formulations, when packaged in an aerosol container, had the pressure in pounds per square inch gauge as shown and all formed clear solutions.

What is claimed is:

1. A composition comprising a solution of 1-naphthylmethylcarbamate in dimethyl ether wherein the weight ratio of 1-naphthylmethylcarbamate to dimethyl ether is within the range of 1:200 to 1:5, wherein the composition is packaged within a pressurized aerosol container.

2. The composition of claim 1 wherein the composition comprises:
from about 0.5 to 20% by weight of 1-naphthylmethylcarbamate;
from about 99.5 to 15% by weight of dimethyl ether; and
from about 0 to 70% by weight of a cosolvent selected from the group consisting of lower alkanols and mixtures of lower alkanols and water.

* * * * *